United States Patent [19]

Barham et al.

[11] 4,360,488
[45] Nov. 23, 1982

[54] REMOVAL OF SOLVENT FROM GELS OF POLY(HYDROXYBUTYRATE) AND SHAPED ARTICLES FORMED THEREFROM

[75] Inventors: Peter J. Barham, Southmead; Alan Selwood, Darlington, both of England

[73] Assignee: Imperial Chemical Industries Limited, London, England

[21] Appl. No.: 174,836

[22] Filed: Aug. 4, 1980

[30] Foreign Application Priority Data

Aug. 13, 1979 [GB] United Kingdom ............... 7928172

[51] Int. Cl.³ .............................................. D01D 5/12
[52] U.S. Cl. ................................ 264/210.1; 264/211; 264/322; 528/502
[58] Field of Search ................... 435/146, 822, 837; 560/185; 528/502; 264/211, 210.1, 322

[56] References Cited

U.S. PATENT DOCUMENTS

| | | | |
|---|---|---|---|
| 2,684,348 | 7/1954 | Dietrich et al. | 260/30.8 |
| 2,963,340 | 12/1960 | Satterthwaite | 264/184 |
| 3,036,959 | 5/1962 | Baptist | 560/185 |
| 3,044,942 | 7/1962 | Baptist | 560/185 |
| 3,242,246 | 3/1966 | Stand | 264/127 |
| 4,127,624 | 11/1978 | Keller et al. | 264/23 |
| 4,137,394 | 1/1979 | Meihuizen et al. | 528/502 |
| 4,140,741 | 2/1979 | Lafferty et al. | 264/184 |

FOREIGN PATENT DOCUMENTS

| | | | |
|---|---|---|---|
| 37-9765 | 7/1962 | Japan | 264/24 |
| 46-38339 | 11/1971 | Japan | 264/164 |
| 6512955 | 5/1966 | Netherlands . | |
| 389173 | 3/1933 | United Kingdom . | |
| 569073 | 5/1945 | United Kingdom . | |
| 603040 | 6/1948 | United Kingdom . | |
| 852525 | 10/1960 | United Kingdom . | |
| 2042414 | 9/1980 | United Kingdom . | |
| 2051667 | 1/1981 | United Kingdom . | |

*Primary Examiner*—Jay H. Woo
*Attorney, Agent, or Firm*—Cushman, Darby & Cushman

[57] ABSTRACT

A process of forming shaped articles comprising forming a free draining gel from a solution of poly(hydroxybutyrate) in a poor solvent under conditions which cause crystallization of the polymer and subjecting the gel to a non-random deformation process so that the associated solvent is expressed. Some residual solvent may be present and can assist in subsequent fabrication processes but the solvent may also be completely removed for such processes. The resulting products have good physical properties, after uniaxial or biaxial drawing.

7 Claims, No Drawings

REMOVAL OF SOLVENT FROM GELS OF POLY(HYDROXYBUTYRATE) AND SHAPED ARTICLES FORMED THEREFROM

This invention relates to the removal of solvent from gels of thermoplastic polymers and to shaped articles formed therefrom.

The formation of gels from polymer solutions has previously been observed in a number of polymeric systems.

By the term "gel" is meant a three-dimensional network of polymer chains in an environment of a different fluid material in which a significant number of the polymer chains contain at least three linking points along their length which are linked to other polymer chains. The polymer chains may be molecular in nature or may consist of fibrils made up of molecular chains.

It has now been found that certain types of gels can be prepared in a form from which the solvent can be readily expressed. These gels are hereinafter termed "free-draining gels". This type of gel provides an intermediate product from which shaped articles can be formed. The gels of this invention may be prepared from homogeneous masses which contain the polymers either in solution or as a swollen mass. Throughout this specification, unless otherwise specified, the term "solution" is used to include homogeneous masses of polymers when in complete solution or when in swollen form, the term "dissolving" is used to include the processes of forming a complete solution and of forming a swollen mass and the term "solvent" is used to describe the material used to form a solution or a swollen mass.

According to the invention there is provided a process comprising forming a free draining gel from a solution of a crystallisable, high molecular weight polymer under conditions which cause crystallisation of the polymer and subjecting the gel to a non-random deformation process. The preferred method of forming a gel in which the polymer contains at least some polymer in crystalline form is by cooling a solution of the polymer to a temperature at which the solution is supersaturated. Normally, the solution is prepared by heating the polymer in a solvent at a temperature above that at which it will crystallise spontaneously from an unstirred solution. It is preferred that the heated solution should be saturated with respect to the polymer at the temperature at which the solution is formed. A gel may also be formed by the addition of an appropriate non-solvent, that is a miscible solvent that will cause a state of supersaturation to occur after the addition to the solution.

The invention provides a useful method of recovering crystallisable polymers from solution or of purifying polymers from impurities present as a result of the polymerisation process. Additionally, the invention provides a useful route to the formation of shaped articles from polymer gels.

Accordingly, there is also provided a shaped article of a crystallisable, high molecular weight polymer formed by subjecting a gel of the polymer to a non-random deformation process and forming the resulting product into a desired shape.

In the three-dimensional gel used in the invention the linking points between the polymer chains may be direct chemical links but at least some of the linking points and preferably the majority, if not all, of the linking points should arise by association of chains through crystallisation. This material differs from the single crystal material described in Journal of Macromolecular Science-Physics B2(2) 337-359 1968 wherein the polymer has been crystallised slowly at high temperature so that the crystals have time to form as separate, unconnected single crystals or multi-layers of such crystals. The difference is most clearly shown by examining the viscosity of he material produced. The gels used in the invention are so viscous that they are capable of supporting a stainless steel ball bearing 1.5 mm in diameter whilst the gel still contains solvent. Suitable gels are also coherent in that they can be picked up ith forceps without the gel disintegrating to any substantial extent. For example, a dilute solution of Hostalen GUR (high molecular weight polyethylene) (0.1 g in 100 ml of xylene) prepared by heating at about 130° C. may be caused to precipitate the polymer in gel or single crystal form by agitating whilst cooling and by cooling without agitating respectively. The product obtained by cooling without agitation was a fine precipitate which would not support a stainless steel ball bearing 1.5 mm in diameter. The precipitate was not coherent and could not be removed from surrounding solvent with forceps. By contrast the product formed with agitation was a gel which would support the 1.5 mm diameter ball bearing and could be removed from the surrounding solvent as an entity using forceps.

The different natures of these precipitates also give rise to differences in properties of products fabricated from the precipitates. Thus the gel after removal of the solvent, can be drawn to a greater extent at a given temperature than a mat formed from the single crystal precipitate. The resulting product from the gel process has a higher modulus than attainable by drawing a mat of the single crystal material.

The non-random deformation process used in the invention is a process in which, for example, the gel is subjected to bulk deformation, such as by pressing the gel between opposed surfaces (as in compression moulding, calendering and extrusion), or to a tensile deformation such as by drawing a fibre or film from the gel. It does not include random deformation processes such as the type of deformation experienced when a gel is sheared in a mixing process. Such mixing may be a process in which mixing vortices are created by the motion of a stirrer or in a process in which the material is effectively cut by rows of pegs or a breaker plate.

British Patent Specification 1 350 487 describes the preparation of polyolefin fibres by a process in which a gel of the polyolefin is subjected to a shear stress so that discrete free floating fibres are formed from the gel. The deformation applied to the gel is a stirring process, that is a random deformation process, which results in discrete free floating fibres. The shear stress applied to the gel results in the formation of unconnected fibres. Although these fiberes may be formed into a shaped article, such as a non-woven sheet, by a subsequent processing step, there is no disclosure of forming a shaped article directly from the gel by applying a non-random deformation process.

U.S. Pat. No. 4,127,624 discloses a process of forming fibres by making a gel from a polymeric solution by cooling the solution by subjecting it to sonic vibrations. The fibres obtained are suggested as being suitable for forming paper or other non-woven fibrous articles. Alternatively it is suggested that the fibrous mass can be impregnated with a curable polymer to provide a fibre reinforced composite. There is no disclosure of subjecting the gel to a non-random deformation to express the solvent from the gel. A process of making high modulus polyolefin fibres from stirred dilute solution is known. See, for example, a publication of A. J. Pennings, Journal of Polymer Science; Polymer Symposium 59, 55–86, 1977. In the process disclosed a polyethylene seed crystal is pushed against the rotor surface of a Couette instrument in which a polyethylene solution is subjected to simple shear flow. Longitudinal growth of the fibrillar crystal is observed.

In the context of this invention the crystallisable polymers are those polymers which are capable of forming a regular, repeating three-dimensional arrangement of polymer chains when a solution of the polymer containing randomly distributed chains is cooled to precipitate the polymer. The extent to which polymer chains are able to rearrange themselves during the cooling process is dependent on several factors such as the chemical nature of the polymer, the molecular weight and distribution of the polymer chains, the rate of cooling and the nature of the solvent. In general, the crystallised products contain appreciable concentrations of amorphous material, that is polymeric material not in the crystalline form. For the purposes of the present invention, it is sufficient for the polymer to be capable of crystallising to only a slight extent although it is preferred that it should be capable of crystallising to the extent of at least 10%. In general, gel formation is enhanced the higher the attainable crystallinity. In particular, whilst it is possible to form gels of a particulate nature from polymers of relatively low molecular weight (weight average molecular weight less than $0.1 \times 10^6$) the gels of higher molecular weight polymers are preferred because they have much better mechanical integrity and are more suitable for forming into shaped articles.

Typical of polymers which exhibit the ability to form crystallites are polyolefins such as poly(ethylene), poly(propylene, high molecular weight poly(esters), including poly(hydroxybutyrate) hereinafter termed PHB, poly(amides), poly(oxymethylenes), poly(tetrafluoroethylene) and isotactic forms of poly(styrene) and poly(methyl methacrylate). The term poly(tetrafluoroethylene), subsequently abbreviated as "TEE polymer" includes polytetrafluoroethylene (PTFE) and copolymers of tetrafluoroethylene with minor amounts (e.g. up to 5% by weight, especially 0.05 to 2% by weight) of other ethylenically unsaturated monomers copolymerisable therewith such as ethylene and hexafluoropropane.

The molecular weight of polymer should be sufficiently high to provide chains which are long enough to permit a significant number of the polymer chains to contain at least three linking points along their length as this is the criterion necessary to the formation of a gel. In practice, the minimum molecular weight necessary to achieve this criterion will depend on the polymer and its readiness to form crystallites. It is desirable that the polymer used should contain species of molecular weight as high as possible to maximise the chances of gel formation through the formation of crystallite links between associated chains. It is not necessary that all the chains of the polymer used should be of high molecular weight material and it has been found that satisfactory gels can be produced with as little as 5% by weight of polymer of high molecular weight with the balance being relatively low molecular weight material. For many commercially available forms of polymers, such as poly(ethylene), poly(propylene) and poly(tetrafluoroethylene), the molecular weight is sufficiently high to present no problem. Thus, the aforesaid materials are commercially available with weight average molecular weight of $0.5 \times 10^6$ or more and these are eminently suitable for use in the invention. On the other hand, the grades of poly(amides), such as nylon 66, or poly(esters), such as poly(ethylene terephthalate), which are commercially available for preparing fibres or for injection moulding into shaped articles generally have weight average molecular weights below $0.1 \times 10^6$ and are much less suitable for use in forming shaped articles according to the invention because the gel formed is particulate in nature and has much less mechanical integrity than the gels of higher molecular weight material.

In order to prepare a suitable gel of the polymer the polymer must be converted into solution or swollen form in the presence of a suitable solvent. The polymer should be in a form in which it has lost any memory of its previous crystalline state. The concentration of polymer used must be sufficiently high so that, on cooling the solution, a state of supersaturation exists and polymer is precipitated. The solution need not be a saturated solution. Preferably, the solutions are formed at an elevated temperature which may be the boiling point of the solvent used. For some polymers it is advantageous to use an elevated temperature which is above the crystalline melting point of the polymer as obtained from a melt of the polymer. For polymers of high crystalline melting point solvents with boiling points in excess of that temperature may not be available. In such circumstances, solutions may be prepared at temperatures above the crystalline melting point by heating the materials in a pressure vessel.

The solvent employed is preferably a material which will form a solution or a homogeneous swollen mass at the elevated temperature but which will precipitate the polymer readily on reducing the temperature.

With some of the high molecular weight polymers it may be difficult to form solutions containing more than about 5% by weight of polymer. For other polymers swollen masses containing as much as 50% polymer may be prepared. In order to provide a commercially useful process it is advisable to use solutions containing at least 0.5% of polymer and preferably to use solutions which are saturated at the temperature used. Solutions which are close to saturation point produce firmer gels than those resulting from unsaturated solutions.

It is generally advantageous to agitate the mixture when forming the solution but more importantly it is advantageous to agitate the solutions during the cooling process because the gel produced has greater mechanical integrity which makes it a much more suitable precursor for forming shaped articles and because agitation may increase the rate at which gel is formed.

The rate at which the solution is cooled from the elevated temperature has little significance if the solution is agitated during cooling. On the other hand, for non-agitated solutions the solution must be quenched through the temperature at which crystallisation is at its maximum rate to a temperature at least below that at which fibrous crystals can grow.

In the case of TFE polymer the material used to swell or dissolve the TFE polymer must be a highly fluorinated material and must be used at an elevated temperature preferably close to the crystalline melting point. The range of suitable materials is very limited. They may have boiling points below the crystalline melting points of the TFE polymers and it is then necessary to carry out the solution or swelling process under pressure. Under such conditions the materials may be above their critical temperatures, behaving like gases rather than liquids. Suitable materials include perfluorodecalin, perfluoromethyl-decalin, perfluorodimethyldecalin, perfluorokerosene, perfluoromethyl cyclohexane, perfluoro(1,3-dimethyl cyclohexane), decafluorobiphenyl, perfluorophenanthrane and perfluorocanthracene.

Solution or swelling of the TFE polymer may be effected by the simple procedure of heating the polymer in the presence of the highly fluorinated solvent although mild agitation may increase the rate of solution. Low concentration solutions (1% of polymer by weight of the solvent) may be achieved in relatively short periods (ca 30 minutes) but it is preferred to form shaped articles from solutions or swollen masses containing at least 5% by weight of polymer. Swollen masses containing up to 50% by weight of polymer may be formed. It may take up to 2 hours or longer to form solutions or swollen masses at such polymer concentrations. After a homogeneous mass has been formed the mass is cooled, conveniently to room temperature. The highly fluorinated solvent may be recovered by washing the sponge-like gel obtained on cooling with inexpensive exchange solvents, such as the fluorinated hydrocarbons known by the trademarks 'Arcton'111 or 'Arcton'113. Alternatively, the solvent may be at least partially removed by pressing the sponge so that a film or sheet is obtained.

The nature of the texture of the polymer product remaining after removing the solvent may be shown by electron scanning microscopy to be highly voided consisting of a plurality of crystalline areas connected by a large number of fibrils. This structure is present after the solvent has been exchanged and before any pressing operation. Although shaped articles having such a structure can be formed having the shape of the vessel in which the dissolution or swelling process was effected it is preferred that shaped articles are formed by subjecting the homogeneous mass to a non-random deformation process, either before or after the fluorinated solvent has been exchanged.

The type of TFE polymer used is not limited to the coagulated dispersion form but also includes, for example, the type known as granular polymer. This has the advantage of not requiring either the hydrocarbon or the fluorinated emulsifier in its preparation. It is also possible to prepare higher molecular weight materials by the granular process. The present invention therefore offers the opportunity of preparing porous shaped articles which are essentially free from impurities which may be introduced with the auxiliary materials used in the polymerisation.

The TFE products described are suitable for the formation of diaphragms for use in electrochemical cells including electrolytic cells. The electrolytic cells for the electrolysis of an aqueous alkali metal chloride solution to give chlorine and an alkali hydroxide (e.g. the electrolysis of brine). For these applications, the structure may suitably be in the form of a sheet or tube, thin porous sheets being preferred. Further electrochemical uses are as battery separators and diaphragms in cells for the recovery of metals. The diaphragms also find utility as filter membranes for a wide variety of uses.

In the case of PHB the solvent should be a poor solvent for PHB. PHB is a naturally occuring linear polyester and is accumulated by many bacteria as granules within the bacterial cells as an energy reserve material. Solid PHB separated from such bacterial cells, for example by solvent extraction followed by precipitation (see for example U.S. Pat. Nos. 3,036,959 and 3,044,942) is a crystalline, or partly crystalline material, melting at about 180° C. Freshly precipitated PHB is partially crystalline and crystallises further on heating to e.g. 100° C. or more. The difference in crystallinity is evident from the solubility characteristics of the polymer. Thus freshly precipitated PHB is soluble in chloroform at room temperature whereas the same material after heating for 30 minutes at 100° C. is not soluble in chloroform at room temperature. Methylene chloride will dissolve freshly precipitated PHB at room temperature only if the PHB has not been allowed to become warmer than about 60° C. after precipitation. Freshly precipitated PHB is not soluble at room temperature in 1,2-dichloroethane even if the precipitated PHB has not allowed to warm to above 40° C. Chloroform, methylene chloride, and 1,2-dichloroethane do however dissolve PHB at elevated temperatures, e.g. under reflux conditions. However poor solvents such as 1,2-dichloroethane can be used to extract PHB from bacterial cells at relatively low temperatures, e.g. 10° to 40° C.: in the state in which PHB exists in the bacterial cells, it is more readily dissolved by such solvents than after the PHB has been precipitated or otherwise separated from a solution thereof. This is presumably due to the configuration of the PHB in the bacterial cells being different to that of PHB precipitated from a solution thereof.

One aspect of the present invention is concerned with the separation of PHB from solutions in poor solvents, such as 1,2-dichloroethane, in which freshly precipitated PHB that has not been heated to above 40° C. is not soluble at temperatures below 25° C. By the term "not soluble" we mean that the solubility of the PHB in the solvent is less than 0.1% by weight. The solutions, which preferably contain 0.5 to 10% by weight of PHB, may be obtained by direct extraction of PHB from the bacterial cells or by dissolution of previously isolated PHB; generally elevated temperatures are required to effect dissolution when using previously isolated PHB. The use of more dilute solutions tends to be uneconomic while more concentrated solutions tend to be difficult to handle because of excessively high viscosities. The preferred solutions contain 1 to 4% by weight of PHB. Where the solutions are made by direct extraction from the bacterial cells, they are preferably filtered before gelation to remove any suspended bacterial fragments.

The solutions may be caused to gel by a number of methods which may be used singly or in combination. Examples of gelation including techniques include:
(i) cooling the solution, e.g., to below 0° C., followed by warming to a temperature below 30° C.;
(ii) shearing the solution, e.g. by stirring and then allowing it to stand at room temperature;
(iii) seeding the solution with previously gelled PHB and then allowing it to stand;
(iv) storage at room temperature.

The time taken to produce a gel depends on, inter alia, the gelation inducing conditions and the concentration of the solution. Thus while a solution may gel simply by storage at room temperature for several days, gelation may be induced in an identical solution by cooling and/or stirring for an hour or two.

In order to produce a gel spontanously on storage at room temperature the concentration of PHB must be at least 1.5% by weight of solvent. For solutions of lower concentration gelation only occurs if an additional step, such as shearing or cooling, is applied.

Coherent gels which are able to support a ball bearing of 1.5 mm diameter are readily obtained using concentrations of 1% or more by weight of PHB. Below this concentration the gel will readily support the ball bearing but it may not be possible to remove a coherent gel from its surrounding solvent using forceps.

The preferred methods of inducing gelatiom of PHB are shearing and/or cooling followed by warming to below 30° C. In the cooling/warming method, the solution is preferably cooled to below 0° C. and then allowed to warm to a temperature within the range 10° to 30° C.

The gels formed from crystallisable polymes by the procedures herein disclosed are unusual in that the solvent is only loosely associated with the polymeric material and will readily drain from the extended gels. Thus, even if left suspended in the solvent liquor, a gel of poly(ethylene) will expel 50% of the solvent originally associated with the polymer over a period of about 2 days. This free-draining nature of gels makes them ideally suited for forming shaped articles by processes in which stress is applied to the gel. Thus, the gel may simply be pressed between opposed surfaces whereupon the solvent is essentially removed leaving a film of polymer. On the other hand, solvent can be expelled using much less severe stress. The internal stresses involved in stretching the gel, such as by drawing fibres from a gel of poly(ethylene), are sufficient to cause substantial quantities of the solvent to be expressed. It is desirable that the non-random deformation process should remove only part of the solvent because some residual solvent is useful in further fabrication of the shaped article in fibre or film form. Thus, films from which essentially all the solvent has been removed by pressing can be uniaxially drawn at room temperature to an extension of 1000 to 1500% of the original length presumably because of the presence of a very small amount of solvent. On the other hand, the same film, if dried in a vacuum oven, is brittle at room temperature. Products from which all the solvent has been removed, for example by drying, can however be readily fabricated at elevated temperatures up to the melting temperature of the polymer.

When these processes include a stage in which the polymer is oriented significant improvements in physical properties may occur which are superior to those obtained by processing other forms of the polymer such as melt processing of the polymer, or processing of single crystal precipitates.

The gels are associated with a high concentration of solvent even when the gel is removed from the solvent liquor in which the gel is initially formed. Processes is pressing the gels to form shaped articles need to take account of this high concentration of solvent. It is useful to carry out a preliminary pressing at moderate pressures between porous or absorbent surfaces. Alternatively, at least one of the surfaces of a pair of platens or other pressing surfaces may have sufficient porosity to enable the solvent to escape and the pressing to be completed in one operation.

On squeezing a PHB gel solvent can be expelled leaving a self-supporting handleable material which, in thin film or sheet form, is somewhat akin to parchment. For convenience this self-supporting handeable material is hereinafter referred to as PHB parchment even though it is not necessarily in film or sheet form.

The parchment may contain a considerable proportion of residual solvent: hence the term PHB parchment includes not only the self-supporting handelable material consisting essentially only of PHB, but also such self-supporting handleable materials containing up to 70% by weight of non-PHB material, e.g. solvent.

The amount of residual solvent in the PHB parchment will depend, inter alia, on the conditions used for the squeezing operation. Since the solvents tend to be relatively volatile, the residual solvent content may rapidly be reduced merely by leaving the PHB parchment to stand, or by drying, preferably at temperatures below 100° C.

In order to squeeze the solvent from the gel a simple press may be used or, alternatively, the gel may be passed between rotating rollers; at least one of the opposed surfaces in the press or at least one of the rollers is preferably porous. Provided the pore size is not too large and/or the gel is not too weak (as is obtained with very dilute solutions), the gel maintains its integrity and substantially no polymer enters the pores. Suitably the pore size is below 25 μm.

The pressure applied during the squeezing operation should be sufficient to expel sufficient of the solvent to give a PHB parchment containing less than 70% by weight residual solvent. Generally the applied pressure need not exceed 50 kg cm$^{-2}$ and is preferably in the range 5 to 50 kg cm$^{-2}$. The squeezing operation is preferably conducted at temperatures in the range 10° to 30° C.

Solid PHB produced by casting from the melt crystallises very rapidly and, indeed it has not heretofore been practical to produce, from a PHB melt, a shaped article of PHB that exhibits only a low crystallinity such that the article can be oriented.

When viewed with an optical microscope, PHB parchments show no signs of granular spherulitic crystallisation. Also even when essentially free of residual solvents, PHB parchment exhibits a much lower melting point, circa 150° C., as measured by differential thermal analysis at a heating rate of 10° C./min than solid PHB prepared by other methods (melting point circa 180° C.).

PHB exhibits relatively poor melt stability with significant amounts of degradation occurring at temperatures near or above its normal melting point of about 180° C. However PHB parchments can be further processed at temperatures below the normal melting point of PHB. Thus parchment in the form of sheets, films, rods, or thin sectioned mouldings can be oriented, either uniaxially or biaxially, e.g. by cold rolling or drawing, preferably at temperatures below 160° C., to give tough films, fibres or other shaped articles. Advantage may be taken of residual solvent in the PHB parchment by conducting the shaping operations at low temperatures, including room temperature, and allowing the residual solvent to evaporate after shaping.

Where the PHB parchment is to be further shaped, a plasticiser such as butylene glycol/adipic acid polymer or tri(isopropyl phenyl)phosphate may be incorporated therein. While the plasticiser may be incorporated merely by immersing the PHB parchment in the plasticizer for sufficient time for the requisite amount, preferably 5 to 30% by weight, of plasticiser to be absorbed, the plasticiser is preferably added to the solution prior to gelation. Alternatively the plasticiser may be added to, and absorbed by, the gelled solution prior to squeezing. During the squeezing operation some plasticiser may be expelled with the solvent but sufficient will be retained in the PHB parchment to render the latter easy to process.

The temperature required for further processing will depend on the nature of the processing operation and on the content of residual solvent and/or plasticiser if any. The optimum temperature may be determined by simple experiment.

After further processing the shaped article may be heated, if desired, to effect crystallisation and to remove any residual solvent.

By suitable design of the squeezing operation, the PHB parchment may be obtained in the form of sheet, film, block, rod, mouldings, fibres, or other shaped articles. While the PHB parchment material tends to be translucent it can be converted to the transparent state by heating under pressure to above 150° C. when solvent free, but at lower temperatures if residual solvent is present. The invention may also be used to make coatings on porous substrates such as paper. By using more dilute solutions of the PHB in the poor solvent, weaker gels may be produced which, when pressed against a porous substrate such as paper, provide PHB parchments firmly adherent to the substrate.

The production of a PHB parchment may also be used as an intermediate step in the production of purified PHB. Thus PHB solutions obtained by extraction from bacterial cells generally contain some dissolved impurities, e.g. pigments and lipids. While some of such contaminants may be retained in the solvent expelled in the squeezing operation, generally some will remain associated with the polymer and contaminate the PHB parchment. Since PHB parchments may be processed without melting such contaminants do not necessarily have to be removed. However where the PHB parchment is an intermediate in the production of purified PHB, the contaminants may be extracted from the PHB parchment, which is preferably in film form, by contact with a suitable contaminant extraction solvent, e.g. methanol or acetone, in which the PHB parchment is not soluble. Thereafter the PHB parchment may be dissolved in a suitable solvent, e.g. chloroform, methylene chloride or 1,2-dichloroethane, using elevated temperatures to effect dissolution as necessary, and further processed, e.g. by precipitation to give PHB powder for use as a melt processable plastics material.

Fillers may be incorporated into the polymer solutions prior to gelation. Because of the way in which the solution is converted into shaped articles, i.e. by gelation followed by squeezing the gel, optionally with further shaping of the squeezed product, fillers that may be used include those that cannot normally be used in melt processed polymers. Examples of suitable fillers include large particle size and/or fibrous fillers such as cellulose and glass fibres.

The invention is further illustrated with reference to the following examples.

EXAMPLE 1

A 0.5% (weight/volume) solution of high molecular weight poly(ethylene) sold under the trade name 'Hostalen' GUR) in xylene (0/5 g polymer in 100 ml total volume) was prepared by refluxing until solution was achieved. The hot solution was allowed to cool in a beaker whilst the solution was stirred eccentrically by hand at about 50 rpm with a glass rod. A gel began to form when the temperature had fallen to 90° C. The gel was a strong, coherent gel and showed a strong tendency to expel solvent at room temperature whilst still in the presence of the surrounding solvent.

The gel was removed from the beaker and lightly pressed between filter papers at a pressure of about 10 KPa for several minutes to remove the major part of the remaining solvent. The film product obtained was then placed between fresh filter papers and put in a press to which a pressure of 50 MPa was applied for 2 minutes. The resulting product was a porous, translucent paper-like film. Infra-red analysis indicated that the film contained less than 1% of solvent by weight of the film.

The film was cold drawn (at room temperature) by pulling in a hand-operated Houndsfield tensometer to a draw ratio of 5 through a yield point at 1.2 MPa. At this stage the product exhibited no detectable X-ray crystalline orientation. The fibre had a tensile modulus of 1.1 GPa in the draw direction measured on an Instron tensile tester at a strain rate of $10^{-4}$ sec$^{-1}$ and a strain of $10^{-3}$.

A different batch of gel of the same polymer was prepared in a similar manner. The resulting film was subjected to draw ratio of 21 in the hand-operated Houndsfield tensometer through a yield point of 4 MPa. The fibre produced showed a normal fibre orientation pattern under X-ray examination and had a tensile modulus of 8 GPa.

A further sample of film prepared by pressing and having a width of 2 cm was rolled between steel rollers under a load of 200 kg. The translucent film became transparent.

EXAMPLE 2

A 0.5% (w/v) solution in xylene of high molecular weight poly(propylene) homopolymer having a melt flow index of 0.8 was prepared by refluxing. On cooling to room temperature, whilst being stirred, a coherent gel with good mechanical integrity was formed. Using the same conditions, except in that the solution was left unstirred during the cooling process, a gel did not form until a period of 18 hours had elapsed. The gel was in the form of a diffuse precipitate.

The procedure was repeated using a concentration of 5% (w/v). A gel was obtained on cooling regardless of whether the solution was agitated during cooling. The gel formed without stirring was not a coherent gel. The gel prepared with stirring during the cooling cycle was extremely tough. Films were prepared by pressing according to the procedure in Example 1. These were highly crystalline in nature.

EXAMPLE 3

A sample of gel prepared as in Example 1 was removed from the excess solvent and reheated at 100.2° C. until it became clear (above 96° C. but below the equilibrium dissolution temperature of 118° C.). A thread was drawn from the surface of the material and wound continuously to give a thread length of 100 m. The fibres were allowed to dry at room temperature for 24 hours. The resulting fibre had a tensile modulus of 0.08 GPa and a reversible strain of 80%. The fibre had an extension to break at room temperature of 2000%.

If instead of direct wind up the fibres are deformed while still yet and hot then the solvent is expelled and fibres of high modulus are made. The amount of deformation occurring is difficult to measure as solvent is being expelled at the same time as the deformation occurs but is between 10 and 50 times. A fibre drawn from the reheated gel at 100.2° C. and stretched by winding up at 1 meter per minute after passing over a metal pin showed a tensile modulus of 12 GPa while a fibre drawn from the surface of the same material and stretched approximately 50 times manually (by gripping with tweezers and pulling apart from 2 cm to 1 m in about 1 second) showed a tensile modulus of 28 GPa.

For comparison purposes normal cold drawn poly(ethylene) has a tensile modulus of 1.5 GPa. Poly(ethylene) drawn to a draw ratio of 20 by drawing at 70° C. has a modulus of about 30 GPa. Poly(ethylene) fibres prepared by the surface growth technique of Pennings (described, for example, in Journal of Polymer Science: Polymer Symposium 59, pages 55 to 86, (1977)) at 110° C. have a tensile modulus of about 30 GPa.

COMPARATIVE EXAMPLE A

A 1% (w/v) solution of poly(methyl methacrylate) (uncross-linked Grade A 'Perspex' solid by Imperial Chemical Industries Limited) in acetone was prepared under reflux. After cooling and allowing to stand overnight the polymer remained in solution. On evaporating part of the acetone, a precipitate formed. A non-sticky gel was removed from the excess solvent. On squeezing between filter papers as in Example 1 it was not found possible to remove any of the solvent. Eventually the gel dried out to a hard pellet of polymer.

EXAMPLE 4

10 mg samples of PTFE (as described in the table below) were placed in heavy-wall Pyrex tubes with 1.5 ml of the solvents described below. The ingredients occupied two thirds of the volume of the tube. After sealing the tubes were placed in an autoclave pressurised to 5 MPa and heated to 330° to 340° C. for 3 hours and then cooled to room temperature. The spongy gel products were removed and examined by optical microscopy. The structures observed are recorded below.

| Tube No. | Polymer | Solvent | Appearance of product |
|---|---|---|---|
| 1 | 'Fluon' 256G* | PFA 9** | Mainly spherulitic |
| 2 | 'Fluon' 256G* | PP 3*** | Mainly fibrous |
| 3 | 'Fluon' CD1# | PFA 9 | About 70% spherulitic |
| 4 | 'Fluon' CD1# | PP 3 | Very small fibres |

*'Fluon' 256G is a high molecular weight form of PTFE of the granular type.
'Fluon' CD1 is a PTFE of the coagulated dispersion type.
**PFA 9 is a perfluoromethyldecalin
***PP 3 is a perfluoro(1,3-dimethylcyclohexane).

The spongy products could be formed into a sheet by pressing between platens.

EXAMPLE 5

5 g polytetrafluoroethylene (of the type sold as 'Fluon' G163 by Imperial Chemical Industries Limited), in the form of small shavings cut from a sheet of sintered skived tape of thickness 50 μm, and 50 g perfluoromethyldecalin were weighed out into a thick-walled Carius tube. The sample was degassed for 30 minutes to remove dissolved gases from the solvent and air bubbles trapped by the polymer. The tube was sealed under vacuum. The Carius tube was sealed in a stainless steel cylinder containing a hydraulic fluid (hydrogenated triisobytylene). The cylinder was heated by electric cuff heaters to 350° C., thus process taking about 3 hours. Above the boiling point of the perfluoromethyldecalin, the pressure generated inside the Carius tube was compensated on the outside by increasing the hydraulic pressure surrounding the Carius tube to prevent the tube from breaking. The pressure generated was approximately 6 MPa.

The sample was left at 350° C. for 3 hours and the heat source was removed; the cooling to room temperature took about 3 hours.

The gel-like sponge polymer was Soxhlet extracted using 'Arcton' 113 (boiling point 45.8° C.) for 6 hours. The extracted sample was dried under vacuum.

Examination of the PFTE by infra-red spectroscopy showed that the crystallinity had increased to 92%, from an original value of 69%. An increase in crystallinity was also inferred from SCS measurements.

Examination of the polymer obtained under electron scanning microscopy showed that it had a very porous structure apparently consisting of crystalline areas interconnected by fibrillar material.

The porous product was formed into a porous sheet by pressing between platens.

EXAMPLE 6

A beaker containing 162 parts by weight of a solution of PHB (about 2.6 parts by weight) in 1,2-dichloroethane, obtained by extracting an aqueous suspension of PHB-containing cells of *Azotobacter chroococcum* with 1,2-dichloroethane at 20° C., was cooled to below 0° C. by immersion in dry ice for 1 hour. The beaker was then removed from the dry ice and allowed to warm to 25° C. The solution was found to have gelled with considerable syneresis. The separated 1,2-dichloroethane (about 32 parts by weight) was decanted off and analysed: its PHB content was less than 0.1% by weight.

The resulting gel (about 130 parts by weight) was then squeezed between wads of absorbent paper in a press at 20° C. using an applied pressure of 10 kg cm$^{-2}$ for 60 seconds.

On opening the press a thin colourless translucent sheet of the pressed gel was obtained. This PHB-parchment (8.2 parts by weight) contained 68% by weight 1,2-dichloroethane and could be lifted from the paper wad. 1,2-dichloroethane evaporated from the PHB-parchment on standing at 20° C.

The solvent content after various times is shown in the following table.

| Time after pressing min | %, by weight 1,2-dichloroethene in the parchment |
|---|---|
| 0 | 68 |
| 3 | 48 |
| 4 | 13 |
| 6 | 7 |

Examination of the PHB-parchment by optical microscopy showed no signs of spherulitic crystallisation.

The PHB-parchment was then dried in an oven at 100° C. for 2 minutes to remove any residual 1,2-dichloroethane. The dried PHB parchment had a melting point of about 150° C. as measured by Differential Scanning Calorimetry at a heating rate of 10° C./min.

The dried PHB parchment was soluble in cold methylene chloride and in hot 1,2-dichloroethane but, after heating to 150° C., followed by cooling, and was then not soluble in cold methylene chloride.

Transparent films were made from the dried parchment by pressing at 150° C. for 1 minute at a pressure of 5 kg cm$^{-2}$.

EXAMPLE 7

Example 6 was repeated save that immediately after removal of the PHB parchment from the wad of paper, it was rolled at 20° C. to give an oriented film.

Samples left exposed to the atmosphere after passing so that the 1,2-dichloroethane content was reduced by evaporating required progressively higher rolling temperature in order to obtain oriented film as the 1,2-dichloroethane content was reduced. A dried parchment required a rolling temperature of 150° C.

EXAMPLE 8

Example 6 was repeated, with similar results, save that the PHB solution was not obtained directly by extraction of the bacterial cells but by dissolving precipitated PHB in hot 1,2-dichloroethane.

By way of contrast similar solutions of PHB in chloroform or methylene chloride could not be caused to gel.

EXAMPLE 9

Gels were formed from 1,2-dichloroethane solutions containing about 2% by weight PHB by a number of techniques. The solution was subjected to a pretreatment and then left to stand at 25° C. until a gel formed. The pretreatments and time to gelation are set out in the following table.

| Pretreatment | Time to gelation (days) |
|---|---|
| none | 10 |
| seeding with gelled PHB | 1 |
| stirring for 10 minutes | 5 (weak gel formed) |
| cooling to below 0° C. for 1 hour | gelation immediate on warming to 25° C. |

The gels could be pressed to give PHB-parchments as in Example 6.

EXAMPLE 10

10 parts by weight of Wolflex BUT, (a high molecular weight polyester of adipic acid and butylene glycol) as a plasticizer were added to 90 parts by weight of a 1,2-dichloroethane solution containing 1.55% by weight PHB. The solution was gelled and pressed as in Example 1 to give a PHB parchment which, after drying at 60° C. for 90 minutes had a plasticizer content of 7% by weight.

The dried parchment was converted into a tough transparent oriented film by rolling at 150° C.

EXAMPLE 11

A PHB gel formed by cooling a solution in dichloroethane in a freezer was pressed between filter papers to expel solvent using a maximum pressure of 20 MPa (i.e. 15 tonnes on a 10 cm diameter disc). The pressed gel had a modulus of ca 1.5 GPa. A specimen 10 mm long cut from the pressed gel film was drawn at 155° C. and 50 mm/min using an Instron tensile testing machine. The draw ratio achieved was 3.8 and the modulus of the drawn material (in the draw direction) was 4.2 GPa.

EXAMPLE 12

A 1% solution of high molecular weight polypropylene in xylene was cooled from 120° C. to room temperature, during cooling it was stirred and formed a gel. The gel was pressed to expel solvent using the same method described in Example 11. A specimen 2 cm long cut from the pressed film was drawn at 120° C. and 50 mm/min in an Instron. A draw ratio of 38 was achieved and the modulus of the drawn material (in the draw direction) was 19 GPa compared with 1.7 GPa for the undrawn material.

Comparative Example B

A 0.1% (w/v) solution of 'Rigidex' 50 polyethylene was crystallized from xylene solution at 80° C. after using the self seeding technique described in Journal of Macromolecular Science-Physics, B2(2) 337–359, 1968 at a seeding temperature of 103° C. The crystals formed were allowed to sediment at room temperature and formed into a mat. The excess solvent was removed and the mat was allowed to dry at room temperature. Tensile specimens having dimensions 1 cm×0.25 cm×0.01 cm were cut from the mat.

The samples were drawn at various temperatures. At 125° C. the maximum draw ratio possible was 31. The drawn product had a modulus of 60 GPa. At 65° C. the maximum draw ratio was 6 and the drawn product had a modulus of 12 GPa.

Considerably higher draw ratios and correspondingly moduli values are obtainable by use of the products obtained from the gel process of the present invention.

EXAMPLE 13

'Hostalen' GUR (a high molecular weight linear polyethylene) (3 g) was dissolved in xylene (400 ml) by refluxing. The hot solution was tipped into a 20 cm diameter Petri dish. The dish was agitated gently as the solution was cooled. On cooling, a gel formed occupying most of the volume formerly occupied by the solvent. The solvent was removed from the gel by pressing a perforated screen into the upturned dish against the gel and subsequently allowing to dry in air for 8 hours. The product obtained was a brittle white sheet showing the presence of some fibrous material and had a thickness between 50 to 100 μm. Infra red analysis showed the absence of xylene.

Square plaques (6 cm×6 cm) were cut from the dried sheet and were biaxially drawn to a ratio of 3:1 simultaneously in both directions. The thin section of the samples prevented the use of high draw ratios. The drawn films were transparent but inhomogeneous because of the fibrous nature of the undrawn sheet. The average thickness of 8 films prepared in this manner was 8.35 μm and the average modulus was 2.4+0.6 GN/m$^2$. Although these figures are considerably higher than normal linear high density polyethylene films prepared from the melt it is anticipated that considerably higher values would be obtained using high draw ratios on thicker initial sheets.

We claim:

1. A process comprising forming a gel from a solution of poly(hydroxybutyrate) in a poor solvent and subjecting the gel to a non-random deformation process.

2. A process according to claim 1 in which the solvent is 1,2-dichloroethane.

3. A process according to either claim 1 or claim 2 in which the non-random deformation process comprises pressing the gel between opposed surfaces.

4. A process according to claim 1 in which the product obtained by subjecting the gel to the non-random deformation is then oriented.

5. A process according to claim 1 in which the product obtained by subjecting the gel to the non-random deformation is fabricated into a shaped article at a temperature below 160° C.

6. A process according to claim 1 in which the non-random deformation process is such as to remove only part of the solvent and the product thereof is fabricated into a shaped article.

7. A process according to claim 1 in which the product obtained by subjecting the gel to the non-random deformation process is subjected to a fabrication step and a plasticizer is incorporated prior to said fabrication step.

* * * * *